(12) United States Patent
Cole et al.

(10) Patent No.: US 9,075,002 B2
(45) Date of Patent: Jul. 7, 2015

(54) TERAHERTZ PROBE ARRAY IMAGING SYSTEM

(75) Inventors: Bryan E. Cole, Cambridge (GB); Simon J. Chandler, Cambridge (GB)

(73) Assignee: TeraView Limited, Cambridge (GB)

( * ) Notice: Subject to any disclaimer, the term of this patent is extended or adjusted under 35 U.S.C. 154(b) by 0 days.

(21) Appl. No.: 10/588,891

(22) PCT Filed: Feb. 11, 2005

(86) PCT No.: PCT/GB2005/000489
§ 371 (c)(1),
(2), (4) Date: Mar. 6, 2007

(87) PCT Pub. No.: WO2005/080947
PCT Pub. Date: Sep. 1, 2005

(65) Prior Publication Data
US 2007/0158571 A1    Jul. 12, 2007

(30) Foreign Application Priority Data

Feb. 13, 2004    (GB) .................................. 0403272.8

(51) Int. Cl.
G01N 21/49        (2006.01)
G01N 21/3581      (2014.01)
G01N 21/47        (2006.01)
G01N 21/3563      (2014.01)
G01N 21/17        (2006.01)

(52) U.S. Cl.
CPC ........ *G01N 21/3581* (2013.01); *G01N 21/3563* (2013.01); *G01N 21/474* (2013.01); *G01N 21/49* (2013.01); *G01N 2021/1772* (2013.01); *G01N 2201/0853* (2013.01)

(58) Field of Classification Search
CPC ........................... G01N 21/3581; G01N 21/49
USPC ...................................................... 250/341.1
See application file for complete search history.

(56) References Cited

U.S. PATENT DOCUMENTS

| 4,654,749 A | 3/1987 | Kanai |
| 4,769,827 A | 9/1988 | Uno et al. |
| 5,251,128 A | 10/1993 | Crawford |
| 5,450,203 A | 9/1995 | Penkethman |
| 5,461,476 A | 10/1995 | Fournier |
| 5,710,430 A | 1/1998 | Nuss et al. |
| 2002/0074500 A1 | 6/2002 | Mickan et al. |
| 2003/0178584 A1 | 9/2003 | Arnone et al. |

FOREIGN PATENT DOCUMENTS

| GB | 2138235 A | 10/1984 |
| GB | 2352512 | 1/2001 |
| GB | 2384555 A * | 7/2003 |
| JP | 2003075251 A | 3/2003 |
| WO | WO 00/75641 A1 | 12/2000 |
| WO | WO 03/042670 A1 | 5/2003 |
| WO | WO-03/102518 | 12/2003 |
| WO | WO 2005/080947 * | 1/2005 |

* cited by examiner

*Primary Examiner* — Marcus Taningco
(74) *Attorney, Agent, or Firm* — Dickstein Shapiro LLP

(57) ABSTRACT

A probe array (1) for an imaging system for examining an object (19) comprising at least one emitter (7) for emitting radiation, a plurality of detectors (9) for detecting radiation and means for directing radiation emitted by the at least one emitter (7) to the object (19) and for directing radiation reflected from the object (19) to at least two of the plurality of detectors (9) wherein in use the emitted radiation is scanned by means (21) across the object (19).

58 Claims, 14 Drawing Sheets

TERAHERTZ PROBE ARRAY IMAGING SYSTEM

The present invention relates to imaging systems for examining objects or samples and is primarily intended for use in the so-called TeraHertz (THz) frequency range which roughly equates to frequencies in the range 25 GHz to 100 THz, particularly those frequencies in the range of 50 GHz to 84 THz, more particularly those in the range from 90 GHz to 50 THz and especially those in the range from 100 GHz to 20 THz.

THz radiation can penetrate most dry, non-metallic, non polar objects such as plastics, and paper and also non-polar organic substances. THz imaging systems have been used in a variety of applications from dermatological imaging to explosives detection. Such systems also have applicability in security scanning and have the benefit that THz photons are of lower energy than those of X-rays. THz photons are also non-ionising.

A proportion of existing THz imaging systems employ single channel THz generation and detection, i.e. the system comprises a single THz emitter and a single THz detector. Such systems are disadvantaged by the fact that in order to construct a full image of a target object the THz beam must be scanned across the whole object. This scanning requires the translation or rotation of optical components, the speed of which translation or rotation is limited by the mechanical limits of whatever motion control system is used.

Existing THz imaging systems are further limited by the rate at which they can capture data. State of the art systems are capable of acquiring approximately 30 000 data-points per second but are limited from acquiring data much above this rate by the intrinsic properties of the system, e.g. the source resistance of the receiver device (a photoconductive antenna).

Existing fixed multiple channel, array based imaging systems are described in EP96300828, US2002067480, US2003184328 and US2002074500.

There is therefore a need for an imaging system and a method of imaging an object which can image an object efficiently and more quickly than prior art systems. It is an object of the present invention to provide an imaging system that substantially overcomes or mitigates problems associated with these prior art systems.

Accordingly this invention provides a probe array for an imaging system for examining an object comprising at least one emitter for emitting radiation, a plurality of detectors for detecting radiation and means for directing radiation emitted by the at least one emitter to the object and for directing radiation reflected from the object to at least two of the plurality of detectors wherein in use the emitted radiation is scanned across the object.

The invention comprises a multi-channel probe array comprising at least one emitter of radiation and a number of detectors. The array is designed such that the object under examination can be raster scanned. This may be achieved either by rotating or moving the object or preferably by providing the array with a raster scanning mechanism for scanning the emitted radiation over the object to be examined. The scanning nature of the multi-channel probe array means that the image acquisition time for imaging large objects can be reduced compared to prior art systems. Further, the fact that an array of emitters/detectors is used also overcomes the problems associated with single channel systems with respect to mechanical limitations of the motion control system.

The probe of the present invention is primarily intended for use in the THz frequency range. Therefore, preferably, the emitter is configured to emit radiation having at least one frequency in the range from 25 GHz to 100 THz. More preferably, the emitter emits pulsed THz radiation, therefore, the emitter is preferably configured to emit pulses of radiation having a plurality of frequencies, at least one of said frequencies being in the range from 25 GHz to 100 THz.

There is no naturally occurring source of coherent THz radiation. However, it is possible to directly generate THz radiation using Gunn diodes and also quantum-cascade lasers. In order to produced pulsed THz radiation the emitter may comprise a frequency conversion member which is configured to emit radiation of the desired frequency in response to irradiation by radiation having a different frequency. Generally, the frequency conversion member is configured to emit radiation which is the difference of the frequency of two or more input beams. To generate THz radiation, a pulsed (i.e. plurality of frequencies) input beam can be used whose frequencies lie in the near infra-red part of the spectrum.

Photoconductive devices (see for example U.S. Pat. No. 5,729,017) can also be used to generate THz radiation, here the emitter comprises a photo-conductive material and an electrode configured to apply a bias across the photo-conductive material, the photoconductive material being configured to emit radiation of the desired frequency in response to irradiation by a pump beam of radiation having at least two frequency components with frequency different to the desired frequency.

A similar detector would comprise a photo-conductive material and an electrode configured to measure a current flowing through the photo-conductive material, the photo-conductive material being configured to generate a current in response to irradiation by a both a probe beam comprising at least two frequency components and a beam of radiation having the frequency which is to be detected.

One possible configuration for the probe array is for a single emitter which is surrounded by the plurality of detectors. For example, the detectors could be arranged in a circle with the emitter as the centre of the circle. Conveniently, this configuration can be used where the probe array is to be mounted within a hand-held unit (a "wand"). Scanning of the object under investigation could then be achieved simply by moving the wand over the surface of the object.

Conveniently, in this configuration the detectors can be arranged so that they are directed towards a single focal point. In use, the probe array would be moved such that the object under investigation would be located at this focal point.

Preferably, the central emitter focuses the emitted radiation into a shaped beam so that the object under examination can be scanned more efficiently.

Alternatively, the wand can further comprise means to direct, by refraction, emitted radiation to the object under examination and backscattered radiation to the detectors. Conveniently, this can be achieved by a suitably configured (multi-faceted) prism.

A second possible configuration for the probe array is to have a substantially equal number of emitters and detectors, i.e. a plurality of emitters as well as detectors. Conveniently, this allows the emitter/detector array to be formed into an extended array which can extend in one or two dimensions depending on the imaging requirements.

For a one or two dimensional array the emitters and detectors can conveniently be formed into an interleaved stack. This thereby allows the emitters to be configured to provide an extended focus of emitted radiation substantially parallel to the probe array. For example, for a vertical stack of emitters/detectors the emitted radiation could be focussed along a vertical axis a short distance from the array. The object to be examined could then be positioned within this extended focus to enable it to be imaged.

For a single dimensional array, scanning of the emitted radiation could either be by linear translation of the whole stack or, preferably, by rotation of the stack of emitters/detectors about an axis through the stack. The latter scanning option allows the emitted radiation beam to sweep out a volume in the vicinity of the object.

Preferably, for a single dimensional array, each emitter and detector is mounted within a self contained housing module and each housing module is arranged to be stackable with similar modules. This facilitates easy customisation of the stack size and permits extra emitters/detectors to be added as required.

In use, each detector will receive reflected radiation from a number of different emitters.

Depending on the particular configuration of probe array used the emitter/detector devices can all be used simultaneously or alternatively can be staggered in their operation. The manner in which the devices are operated will depend on whether interference between neighbouring devices is tolerable/desirable or whether radiation from one particular device should not interfere with neighbouring devices. The "interleaved array" and "wand" configurations above both exploit the fact that radiation from one emitter may be detected by more than one receiver and that one receiver may detect radiation from more than one emitter. Therefore in these configurations all emitter/receiver devices are conveniently operated simultaneously.

For probe arrays that use an irradiating radiation source the array preferably further comprises a lens array to focus the irradiating radiation onto the probe array. For probe array configurations with individually housed emitters and detectors this lens array conveniently comprises a single lens structure. For extended arrays of emitters and detectors the lens array is also of extended scope to match the probe array.

Conveniently, optical fibres can be used to supply the irradiating radiation and for extended arrays a separate optical fibre can be used to supply each emitter or detector device. Where the probe array utilises optical fibres the lens array will be positioned between the ends of the optical fibres and the probe array.

Conveniently, the optical fibre(s) can be mounted in a drilled or etched plate to provide stability to the construction of the probe array and also to ensure the fibres are aligned correctly. Suitable materials for the mounting plate are silicon or zirconium.

The multi-channel probe array also comprises means for directing emitted radiation to the object under examination and for directing reflected radiation back to some or all of the detectors. Conveniently, for THz emitters/detectors, the array comprises a suitably shaped THz transmitting material to couple any THz radiation into or out of the probe array. Suitable materials are polythene, polypropylene, silicon, alumina, aluminium, aluminium nitride, aluminium carbide, silicon nitride, germanium, paraffin-wax or any other suitable polymer, ceramic or semiconductor.

In a further aspect to the present invention there is provided an imaging system for examining an object comprising an imaging system for examining an object comprising a probe array as described above and signal processing means for analysing the radiation detected by the probe array.

A complete imaging system is provided comprising a multi-channel probe array as described above and signal processing means for analysing the output of the detectors. The array like nature of the system allows quicker imaging of a target object and the scanning ability of the system allows larger objects to be completely imaged.

Where the probe array requires irradiation for its operation the system can conveniently further comprise a source of electro-magnetic radiation for irradiating the probe array. The irradiating radiation can conveniently be directed to the probe array by means of a number of optical fibres.

The irradiating source can be coupled to the optical fibres either by means of an arrangement of beam-splitters and fibre couplers (e.g. OEMs) or by means of an array of lens structures, wherein each optical fibre is located at the focal point of one of the lens structures. The latter coupling mechanism is preferable for a large number of optical fibres (e.g. more than 20) since the first coupling mechanism requires each fibre coupler to be independently aligned which is time consuming.

In one embodiment of the imaging system, the probe array is configured as a hand-held unit and the source and signal processing means are housed in a base unit, the hand-held unit and base unit being in optical connection by way of an optical fibre bundle.

In a still further aspect of the invention there is provided a method of examining an object, the method comprising:
emitting a beam of radiation from at least one emitter, said emitted radiation being in the THz frequency range;
directing the emitted radiation to irradiate an object
directing radiation reflected from the object into some or all of a plurality of detectors Embodiments of the invention will now be described, by way of example only, with reference to the following figures in which.

Figure 1:
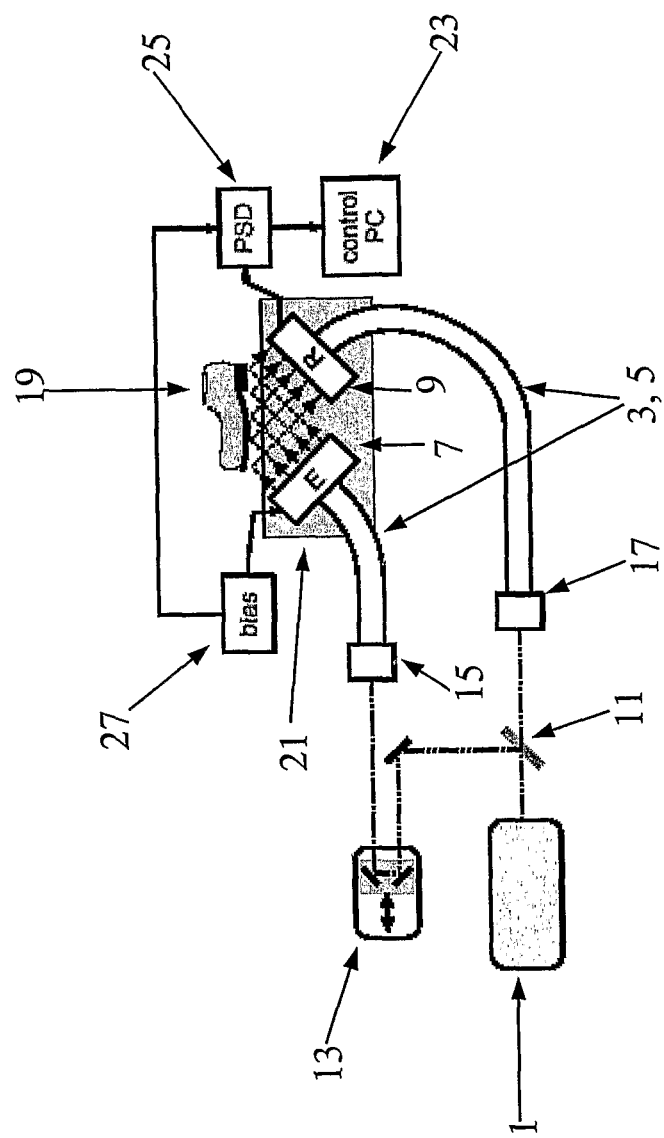
FIG. 1 shows a schematic representation of an array based THz imaging system.

Turning to FIG. 1, a pulsed laser 1 supplies near infra-red (NIR) pulses into two optical fibre bundles (3, 5) that are connected to a THz emitter array device 7 and a THz receiver array device 9. A beam-splitter 11 is used to split the NIR beam into two. An optical delay-line 13 is also included in the emitter path (also called the "pump" beam). Multi-fibre couplers (15, 17) are used to couple the NIR beam into the fibre bundles (3, 5). The emitter array 7 and receiver array 9 are positioned such that THz radiation emitted by the emitter is directed towards an object 19 to be examined (in this case diagrammatically represented as a shoe) and reflections from the object 19 are detected by the receiver array 9. The emitter and receiver arrays are mounted upon a raster scanning system 21 which, in use, allows the emitted THz radiation to be scanned across the object 19 under examination.

A bias voltage 27 can also be directed into the emitter array. Where an ac-modulated bias is used, the output signals from the receiver array are received by a control PC 23 by way of a phase-sensitive detector (PSD) 25. The phase-sensitive demodulation may be performed within the PC or an external demodulating device such as a multi-channel lock-in amplifier used. Alternatively, if a static or largely static bias is used no PSD is required and the output signal may be recorded directly.

Figure 2:
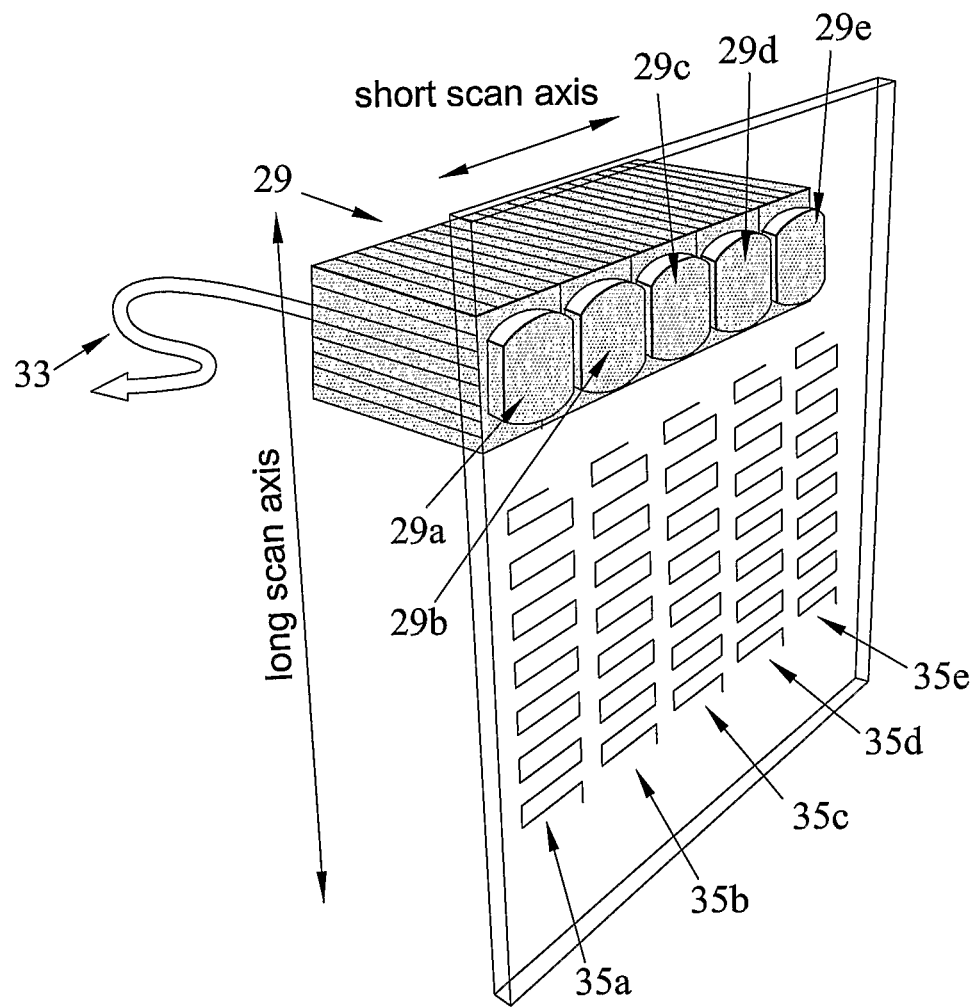
FIG. 2 shows a multi-channel imaging system according to the present invention.

FIG. 2 shows a multi-channel imaging system in which a multichannel transceiver array 29 is composed of five single channel transceiver modules (29a, 29b, 29c, 29d, 29e), i.e. each module comprises one emitter/receiver pair. A THz transparent window 31 separates the transceiver array 29 from the object under examination (not shown). An optical fibre bundle 33 connects the array 29 to the control electronics (not shown).

In use the array 29 is raster scanned across the object under examination. By using five modules in series the distance traveled by each module along the short scan axis is reduced compared to a single module scanning system. The trajectory (35a . . . 35e) of each module is shown schematically.

Figure 11:
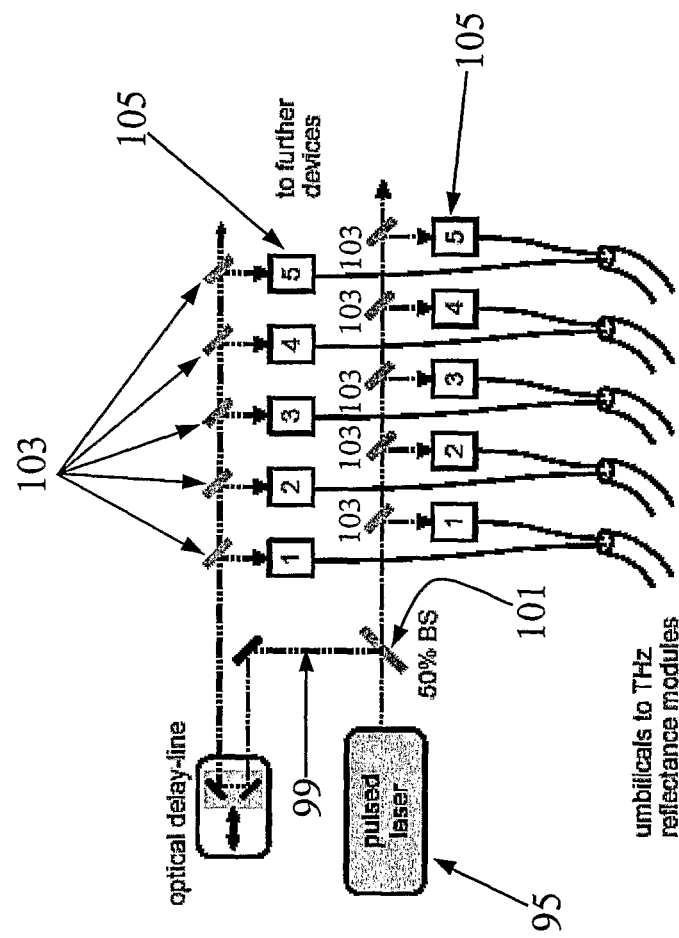
FIG. 11 shows an arrangement for a multi-channel fibre-coupled system.

The probe array configuration (five modules of one emitter/receiver pair) requires that the THz emitted by one module should not interfere with the receiver of any other modules. Therefore this configuration is conveniently operated by staggering the operation of each module so that there is no interference. A suitable scheme for creating staggered device operation is shown in FIG. 11.

Figure 3:
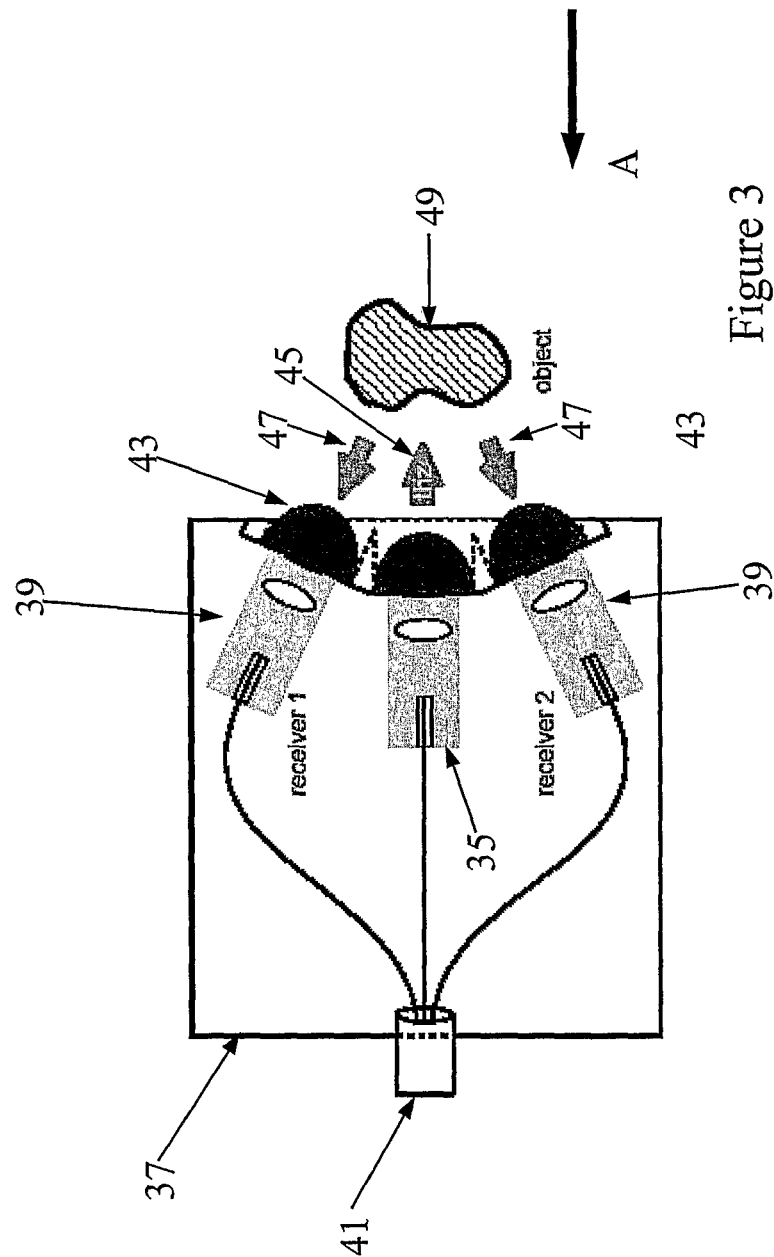
FIG. 3 shows a schematic of a hand-held probe system.

FIG. 3 shows an embodiment of the invention which is particularly suited to the use in a hand-held probe. In this case an emitter 35 is mounted centrally within a transceiver head 37. Multiple receivers 39 are mounted around the emitter 35. In the interests of clarity only two receivers are shown in the Figure which represents a cross-section through the device. If viewed along line A (in the plane of the paper) the receivers would be seen to form a circle around the central emitter. The emitter 35 and each receiver 39 is connected to the control system which for a hand-held system would be located within a remote base unit (not shown). In this case this connection is via optical fibres 41.

Each emitter/receiver 35, 39 includes a lens 43, typically made of silicon or any other THz transmitting material. The lens serves to shape THz emitted from the emitter into a forward directed beam 45 which may or may not be diverging.

The emitter is configured to emit THz radiation at an area of an object to be examined. The THz receivers detect reflected radiation 47 from the object 49.

In use the emitted beam will typically illuminate between 0.1 to 100 cm$^2$ of the target object. Each receiver only captures a portion of the backscattered radiation but the multiple receiver design ensures that a large portion of the backscattered radiation is detected by the probe.

Figure 4:
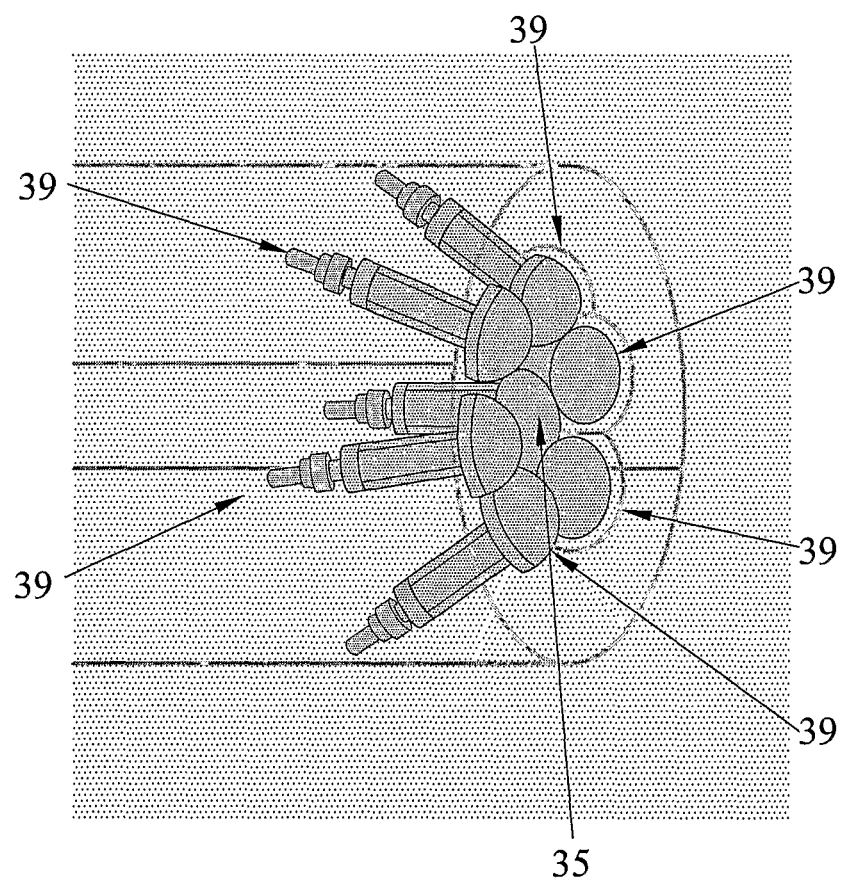
FIG. 4 shows a 3-dimensional rendering of the device of FIG. 3.

FIG. 4 shows a 3-dimensional rendering of the probe depicted in FIG. 3 above. Note that like features are represented by like numerals. The probe has a central emitter 35 device surrounded by six receiver modules 39. Supporting hardware has been omitted for clarity.

Figure 5A:
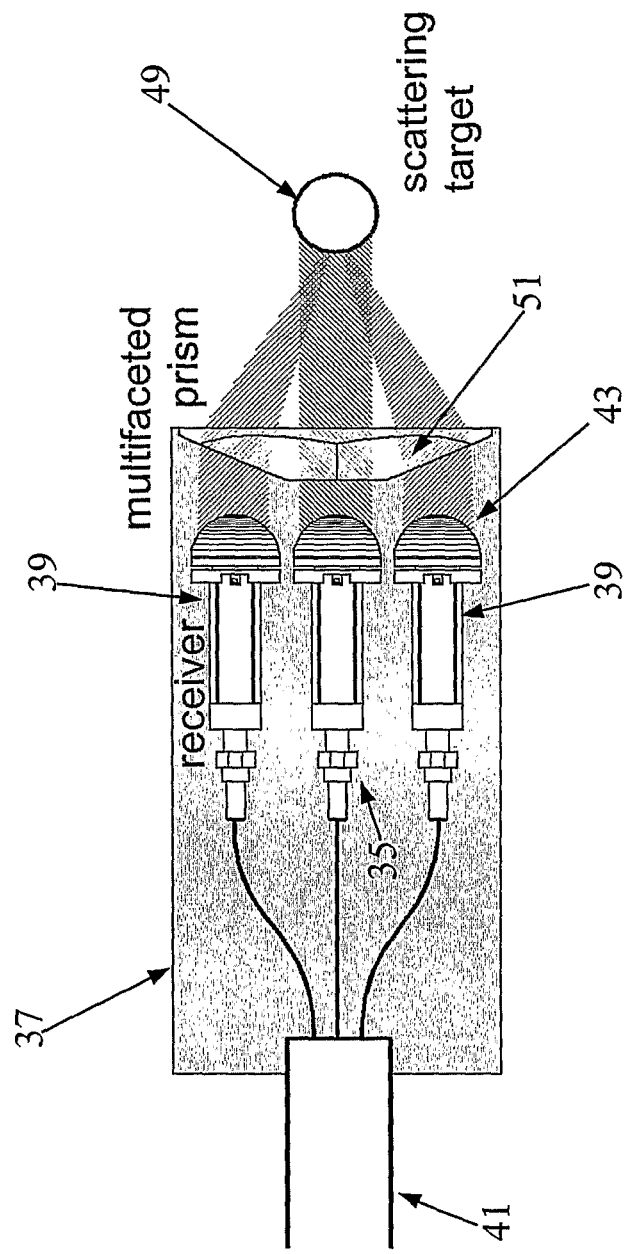
FIGS. 5A and 5B show a variation of the hand-held probe system.

FIG. 5a shows a variation of the hand-held probe embodiment of the invention shown in FIG. 3 (like numerals are again used to denote like features). In this case the emitters 35 and detectors 39 are arranged to be parallel to one another. A multifaceted prism 51 lens is located between the emitter/detectors and the object to be examined. This design of handheld probe is more compact than the variation depicted in FIG. 3.

In use, the prism 51 steers each THz beam (both the outgoing source radiation and the backscattered THz radiation from the object) by refraction. In the Figure, these beams are denoted by the hatched areas. The prism can be made of any THz transmitting material such as silicon, germanium, ceramic (alumina, aluminium-, silicon-, or boron-nitride etc), polythene, polypropylene, silicone and other polymers.

Figure 5B:
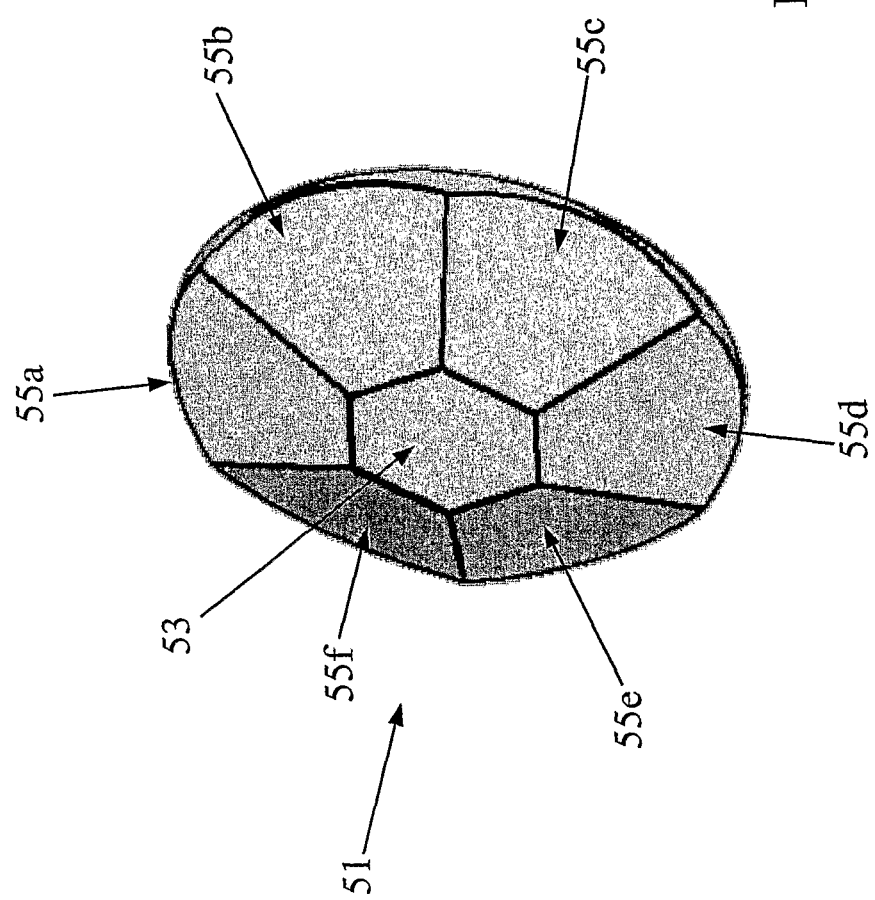

FIG. 5B shows the prism 51 in greater detail. A central facet 53 through which the emitted radiation is steered is surrounded by six angled facets (55a . . . 55f) which couple backscattered radiation from the object to the detectors.

Figure 6:
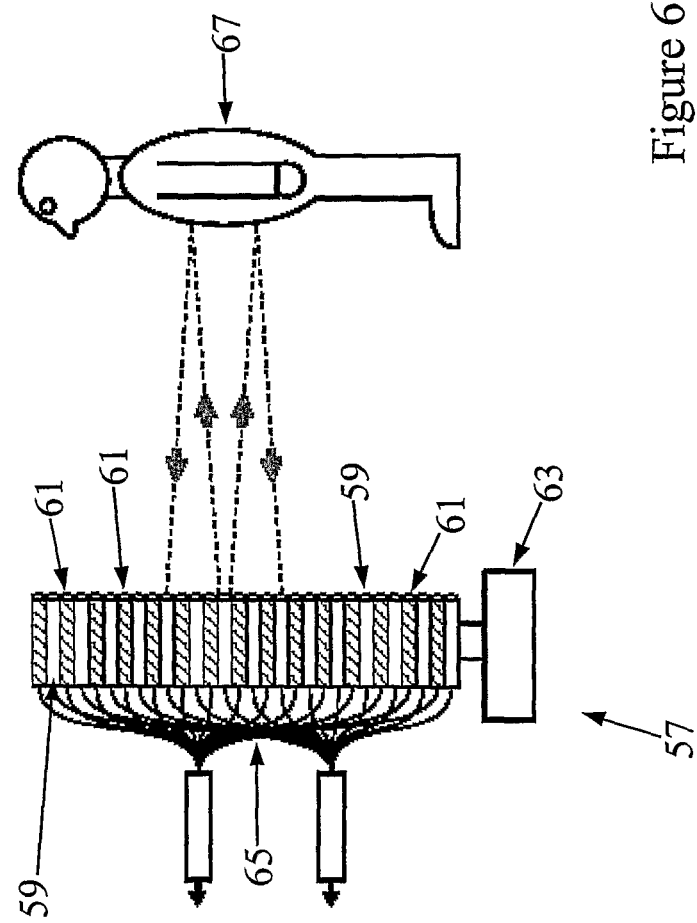
FIG. 6 shows a variant of the invention with a vertical array of emitter/receiver modules (side view)

FIG. 6 shows a multi-channel array 57 of alternating and interleaved THz emitter and receiver modules 59, 61 (Emitter modules are shown with a clear background and receiver modules are shown with a hatched background). The array 57 has been formed into a 1-dimensional stack, which in this case has been arranged vertically. The array 57 is mounted on a scanning system 63 in order to direct the emitted THz radiation. The emitter/receiver modules are connected via optical fibres 65 to the control electronics.

The emitters 59 are configured to create a vertically extended focus at the subject 67 which is typically at a distance of approximately 1 meter from the array. THz radiation back-scattered or reflected from the subject will be received by a number of THz receivers 61 either side of the emitter (beam paths only are shown for the sake of clarity). Typically, each receiver 61 will receive scattered THz originating from approximately two or three emitters 59 either side of it. Signals from the receivers are combined computationally in the control computer (not shown) in order to resolve the subject image along the long axis of the array.

Figure 7:
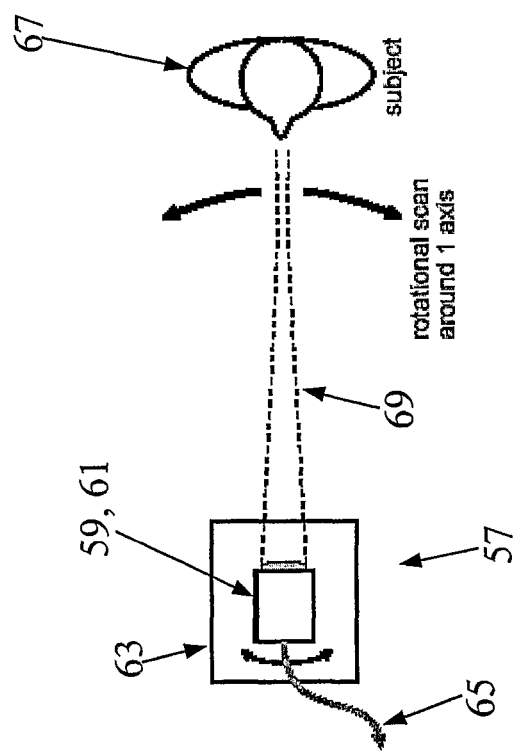
FIG. 7 shows a plan view of the system depicted in FIG. 6.

FIG. 7 shows the multi-channel stack arrangement of FIG. 6 from a plan view. Like features are represented with like numerals. Additionally the THz beam 64 is shown focussing on the subject 67. The array is raster scanned by rotating about its vertical axis such that the THz beam 69 sweeps out a volume in the vicinity of the object 67 under examination. Although rotation of the stack is shown here it should also be noted that the beam could be raster scanned by linear translation of the array stack (e.g. in this case by moving the stack along a line parallel to the side of the page).

Figure 8:
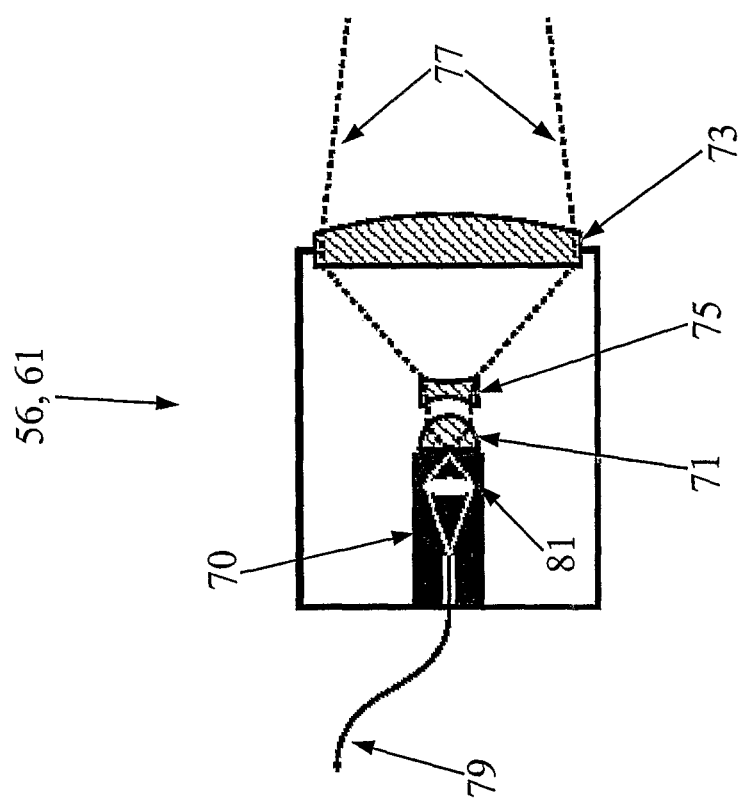
FIG. 8 shows the layout of a single emitter/receiver module from the array of FIG. 6.

FIG. 8 depicts an individual emitter/receiver 59, 61 module from the array of FIGS. 6 and 7 wherein a THz emitter (or receiver) 70 abuts a collimating ellipsoid lens 71 which is generally made from silicon or some other material largely transparent to THz radiation. These components are mounted within a housing which is arranged to be stackable with similar units. Typical dimensions for this housing are 1 cm deep and approximately 6 cm per side. A second, cylindrical or ellipsoidal lens 73 is located in one side of the housing and a third concave lens 75 is located within the housing between the collimating ellipsoid and the lens in the wall of the housing.

In use, the ellipsoid lens 71 collimates any outgoing THz radiation into an approximately 1 cm diameter beam which is then spread laterally using the (concave) lens 75. The diverging THz beam is then re-focussed into the horizontal plane and onto the subject using the lens 73. This lens 73 can be cylindrical, spherical or some other aspheric profile. The beam profile 77 is shown.

NIR radiation is supplied to the THz device by way of an optical fibre 79. A lens 81 focuses the NIR radiation onto the THz device.

Figure 9:
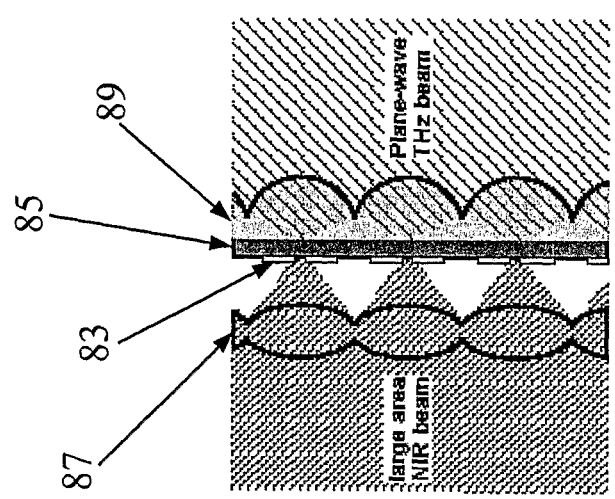
FIG. 9 shows an arrangement for coupling THz antennas to a NIR radiation source.

An arrangement for coupling a free-space beam of NIR radiation onto an array of THz device is shown in FIG. 9. There is no need for any optical fibre connections in this arrangement. THz devices 83 are mounted upon a GaAs substrate 85. A micro-lens array 87 is placed above the THz devices such that the devices are at a focal point of the micro-lens array. A THz macro-lens array 89 is placed on the opposite side of the device substrate.

The micro-lens array 87 has a lens pitch matching the device spacing on the substrate 85. The THz macro-lens array 89 is made from any THz transmitting material such as polythene, polypropylene, silicon, alumina, aluminium, aluminium nitride, aluminium carbide, silicon nitride, germanium, paraffin-wax or any other suitable polymer, ceramic or semiconductor.

In use the micro-lens array 87 couples a large area NIR beam into the array of THz devices 83. The THz macro-lens array 89 couples any THz radiation either in or out of the device (depending on whether the device is an emitter or a receiver). The THz macro-lens array has an equal pitch spacing to the micro-lens array and THz device array.

Additionally, a thin layer of paraffin or silicone may be inserted between the substrate and THz macro-lens array in order to reduce stray THz reflections.

Figure 10:
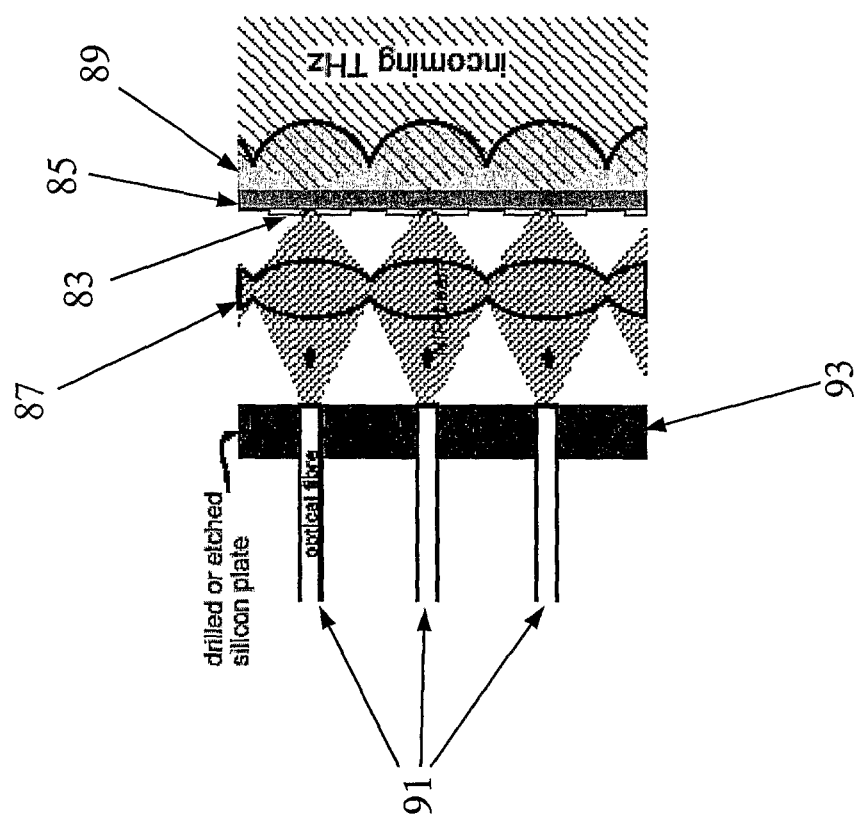
FIG. 10 shows a further arrangement for coupling THz antennas to a NIR radiation source.

FIG. 10 shows a similar arrangement to FIG. 9 (and like features have therefore been represented by like reference numerals). However, this arrangement further includes a group of optical fibres 91 which are mounted on a drilled or etched plate 93 (which is usually constructed of silicon or zirconia).

In use NIR radiation is supplied via the group of optical fibres which are coupled into the THz array by means of the micro-lens array 87. The micro-lens array is arranged to focus the NIR emanating from the fibres into the THz device array.

The arrangement of FIG. 10 allows a 1 or 2 dimensional array of optical fibres to be coupled into a 1 or 2 dimensional array of THz emitters/receivers. This arrangement is similar to the coupling arrangement depicted in FIG. 8 but for multiple fibres/devices instead of a single fibre/device.

In order to use a single laser system to drive multiple THz devices it is necessary to have a means for coupling optical excitation beams from the laser into the fibres of the THz devices. FIG. 11 shows a simple arrangement in which a pulsed laser 95 supplies a laser beam which is split into two paths (pump beam 97 and probe beam 99) by a 50% beam-splitter 101. Following this split the beams are further split using a series of "pick-off" beam-splitters 103. These "pick off" beam-splitters split a small fraction of the main beam into a conventional free-space-to-single mode fibre coupler 105. Each fibre coupler is a standard OEM.

As noted above the arrangement shown in FIG. 11 is suitable for introducing a staggered time delay into the operation of each THz device. Since both the pump beam 97 and probe beam 99 have a number of beam-splitters 103 in series the optical path length will increase along the series of devices. As depicted in FIG. 11 each pair of fibre-couplers (labelled "1" to "5") will experience a longer total optical path length than the fibre-coupler pair to its left (Note: the relative time delay between emitter and detector is the same in each case).

Therefore, in use, the THz devices will receive the optical excitation beam at different times and therefore the devices will be operated in a staggered fashion.

Figure 12:
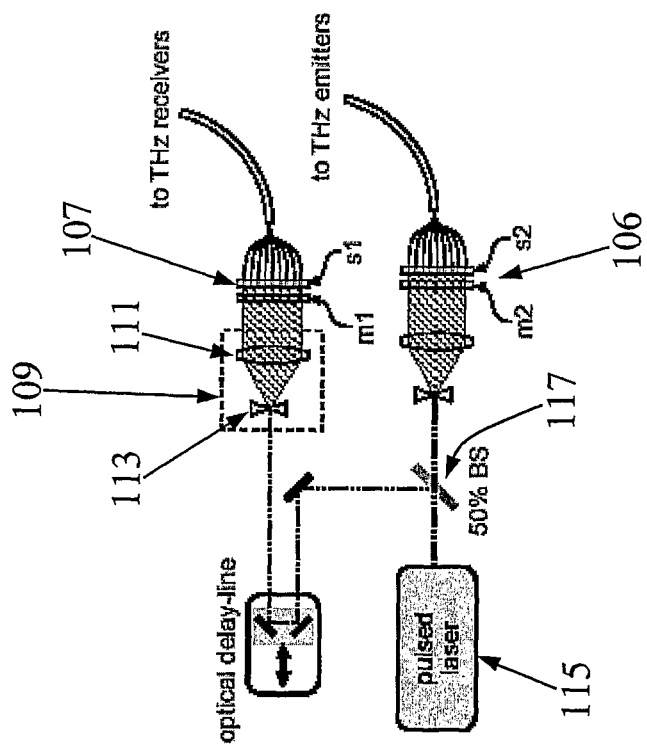
FIG. 12 shows a further arrangement for a multi-channel fibre-coupled system.

The arrangement in FIG. 11 is suitable only for small to moderate numbers of fibres (up to approximately 20 fibres) since each coupler needs to be aligned by hand. An alternative arrangement is shown in FIG. 12. In this case a pair of fibre arrays 106, 107 supplies a number of THz emitters and receivers (not shown). Each 1D or 2D array of optical fibres is mounted in a drilled or etched plate.

For each optical fibre array, a micro-lens array with a pitch arranged to match that of the fibre array is mounted next to the ends of the fibre array such that the fibre ends are located at the focal point of the array. A beam expander 109 is placed on the opposite side of the micro-lens array from the fibre array. Each beam expander comprises a convex lens and concave lens 113.

A pulsed laser 115 provides a source of NIR radiation which is directed into each beam expander via a series of beam-splitters and mirrors.

In use, the pulsed NIR beam is split into two beams by the beam-splitter 117 and directed into the beam expanders which expand the incident NIR beam such that each micro-lens array is illuminated uniformly. The micro-lens arrays focus the NIR beams into the ends of each optical fibre in the optical fibre arrays. These fibres are connected to a series of THz emitters and receivers.

Uniform illumination of a micro-lens array may be achieved using a 'Gaussian to flat-top beam converter' (GFTC). Such devices convert the Gaussian beam profile typically obtained in free-space optical systems to a "flat-top" profile which has a uniform beam intensity over a defined beam area. GFTC devices are a standard optical component and are widely available.

This micro-lens array is an example of a system where similar optical path lengths are used for each device and where each device will therefore be operated simultaneously.

Figure 13:
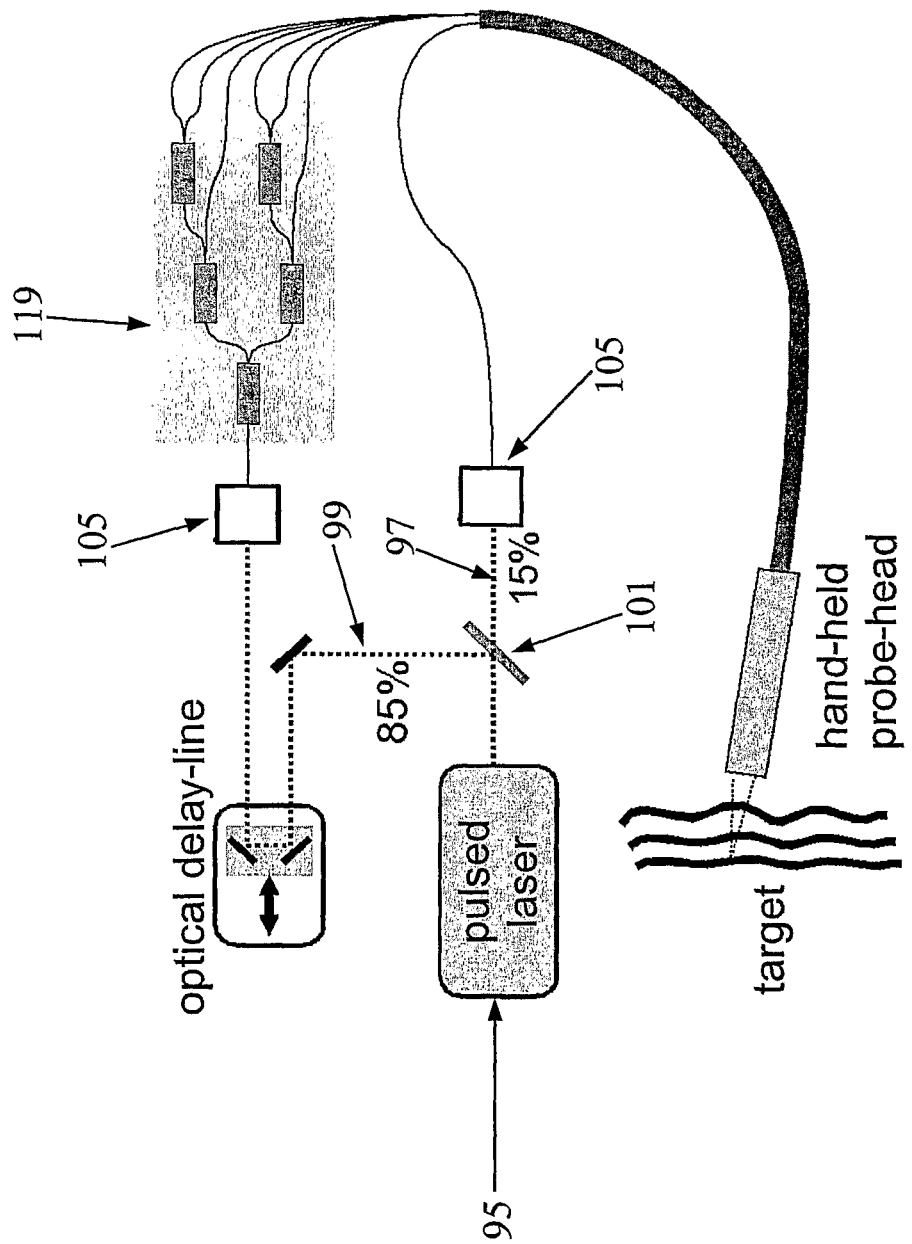
FIG. 13 shows a variation of the arrangement of FIG. 11 with the probe device of FIGS. 3 to 5.

FIG. 13 shows a variation on the arrangement shown in FIG. 11 for a multi-channel fibre coupled system. This arrangement is suitable for use with a hand-held device similar to those described in FIGS. 3 to 5 above. In this case, the pump beam is again split into two paths (pump beam 97 and probe beam 99). However, in this case, the probe beam is subsequently divided via a fibre power-splitter 119 to feed the plurality of receiver devices in the wand. While this method removes the need for the independent alignment of a large number of fibre-coupling devices (as in FIG. 11), the cost of a multi-way fibre-splitter becomes prohibitive for division across many fibres.

The invention claimed is:

1. An imaging system for examining an object, said system comprising:
    a probe array and a scanning mechanism, said probe array comprising:
        a plurality of emitters of THz radiation, and
        a plurality of photoconductive detectors for detecting radiation, the plurality of photoconductive detectors and emitters being arranged in a one-dimensional array along a first axis,
    the probe array being configured such that radiation emitted by at least one emitter of the plurality of emitters is directed to the object and reflected back from the object to at least two of the plurality of detectors;
    the plurality of emitters being further configured to create an extended focus at the object which extends in a direction parallel to the first axis; and
    said scanning mechanism being configured to rotate or move said probe array such that a beam of the emitted radiation is scanned, in a direction orthogonal to said first axis, across the object, and reflected back to said at least two of the plurality of detectors.

2. An imaging system as claimed in claim 1 wherein the at least one emitter comprises a frequency conversion member which is configured to emit radiation of the desired frequency in response to irradiation by radiation of a different frequency.

3. An imaging system as claimed in claim 2 wherein the array further comprises a lens array to focus the irradiating radiation onto the at least one emitter and plurality of detectors.

4. An imaging system as claimed in claim 2 wherein the irradiating radiation is supplied by means of a number of optical fibres.

5. An imaging system as claimed in claim 4 wherein a separate optical fibre supplies irradiating radiation to a single emitter/detector.

6. An imaging system as claimed in claim 4 wherein the array further comprises a lens array that is located between the optical fibres and the at least one emitter and plurality of detectors and wherein only a proportion of the total number of emitters and detectors are in use at any given time.

7. An imaging system as claimed in claim 2 wherein the array further comprises a THz transmitting array to couple in or out any THz radiation.

8. An imaging system as claimed in claim 7 wherein the THz transmitting array is constructed from any of the following; polythene, polypropylene, silicon, alumina, aluminum, aluminum nitride, aluminum carbide, silicon nitride, germanium, paraffin-wax or any other suitable polymer, ceramic or semiconductor.

9. An imaging system as claimed in claim 1 wherein the at least one emitter is a photoconductive device.

10. An imaging system as claimed in claim 1 wherein the at least one emitter is configured to emit radiation having at least one frequency in the range 25 GHz to 100 THz.

11. An imaging system as claimed in claim 1 wherein the at least one emitter is configured to emit pulses of radiation having a plurality of frequencies, at least one of said frequencies being in the range from 25 GHz to 100 THz.

12. An imaging system as claimed in claim 1 wherein the array further comprises means for raster scanning the emitted radiation.

13. An imaging system as claimed in claim 1 wherein the array comprises a single central emitter surrounded by the plurality of detectors.

14. An imaging system as claimed in claim 13 wherein the plurality of detectors are directed towards a point such that in use the object is located at this point.

15. An imaging system as claimed in claim 13 wherein the central emitter directs the emitted radiation into a directed beam.

16. An imaging system as claimed in claim 1 wherein the array comprises a substantially equal number of emitters and detectors.

17. An imaging system as claimed in claim 16 wherein the array is formed into a two dimensional array of emitters and detectors.

18. An imaging system as claimed in claim 16 wherein the array is formed into a one dimensional stack of interleaved emitters and detectors.

19. An imaging system as claimed in claim 18 wherein the emitters are arranged in use to form an extended focus of emitted radiation substantially parallel to the array.

20. An imaging system as claimed in claim 18 wherein the array is raster scanned by linear translation of the stack.

21. An imaging system as claimed in claim 18 wherein the array is raster scanned by rotation about an axis through the stack of emitters and detectors.

22. An imaging system as claimed in claim 18 wherein each emitter and detector is mounted within a self contained housing module.

23. An imaging system as claimed in claim 22 wherein each module is capable of forming a stack with similar modules.

24. An imaging system as claimed in claim 1, further comprising a signal processor for analyzing the radiation detected by the probe array.

25. An imaging system for examining an object as claimed in claim 24 further comprising a source of e/m radiation for irradiating the probe array.

26. An imaging system as claimed in claim 25 wherein the source provides a beam of radiation and the system further comprises a series of beam-splitters and fibre couplers, each beam-splitter being arranged to couple a proportion of the beam of radiation via a fibre coupler into an optical fibre such that in use the optical fibre irradiates the probe array.

27. An imaging system as claimed in claim 25 wherein the source provides a beam of radiation and the system further comprises a lensing array, the array being arranged in use to couple a proportion of the beam into an optical fibre such that the fibre irradiates the probe array.

28. An imaging system as claimed in claim 24 wherein the probe array is configured as a hand-held unit and the source and signal processor are housed in a base unit, the hand-held unit and base unit being connected via optical fibre.

29. An imaging system as claimed in claim 1 wherein only a proportion of the total number of emitters and detectors are in use at any given time.

30. An imaging system for examining an object, said system comprising:
    a probe array and a scanning mechanism, said probe array comprising:
        a plurality of emitters of THz radiation, and
        a plurality of photoconductive detectors for detecting radiation, the plurality of photoconductive detectors and emitters being arranged in a one-dimensional array along a first axis,
    the probe array being configured such that radiation emitted by at least one emitter of the plurality of emitters is directed to the object and reflected back from the object to at least two of the plurality of detectors;
    the plurality of emitters being further configured to create an extended focus at the object which extends in a direction parallel to the first axis; and
    said scanning mechanism being configured to rotate or move said object such that a beam of the emitted radiation is scanned, in a direction orthogonal to said first axis, across the object, and reflected back to said at least two of the plurality of detectors.

31. An imaging system as claimed in claim 30 wherein the at least one emitter comprises a frequency conversion member which is configured to emit radiation of the desired frequency in response to irradiation by radiation of a different frequency.

32. An imaging system as claimed in claim 31 wherein the array further comprises a lens array to focus the irradiating radiation onto the at least one emitter and plurality of detectors.

33. An imaging system as claimed in claim 31 wherein the irradiating radiation is supplied by means of a number of optical fibres.

34. An imaging system as claimed in claim 33 wherein a separate optical fibre supplies irradiating radiation to a single emitter/detector.

35. An imaging system as claimed in claim 33 wherein the array further comprises a lens array that is located between the optical fibres and the at least one emitter and plurality of detectors and wherein only a proportion of the total number of emitters and detectors are in use at any given time.

36. An imaging system as claimed in claim 31 wherein the array further comprises a THz transmitting array to couple in or out any THz radiation.

37. An imaging system as claimed in claim 36 wherein the THz transmitting array is constructed from any of the following; polythene, polypropylene, silicon, alumina, aluminum, aluminum nitride, aluminum carbide, silicon nitride, germanium, paraffin-wax or any other suitable polymer, ceramic or semiconductor.

38. An imaging system as claimed in claim 30 wherein the at least one emitter is a photoconductive device.

39. An imaging system as claimed in claim 30 wherein the at least one emitter is configured to emit radiation having at least one frequency in the range 25 GHz to 100 THz.

40. An imaging system as claimed in claim 30 wherein the at least one emitter is configured to emit pulses of radiation having a plurality of frequencies, at least one of said frequencies being in the range from 25 GHz to 100 THz.

41. An imaging system as claimed in claim 30 wherein the array further comprises means for raster scanning the emitted radiation.

42. An imaging system as claimed in claim 30 wherein the array comprises a single central emitter surrounded by the plurality of detectors.

43. An imaging system as claimed in claim 42 wherein the plurality of detectors are directed towards a point such that in use the object is located at this point.

44. An imaging system as claimed in claim 42 wherein the central emitter directs the emitted radiation into a directed beam.

45. An imaging system as claimed in claim 30 wherein the array comprises a substantially equal number of emitters and detectors.

46. An imaging system as claimed in claim 45 wherein the array is formed into a two dimensional array of emitters and detectors.

47. An imaging system as claimed in claim 45 wherein the array is formed into a one dimensional stack of interleaved emitters and detectors.

48. An imaging system as claimed in claim 47 wherein the emitters are arranged in use to form an extended focus of emitted radiation substantially parallel to the array.

49. An imaging system as claimed in claim 47 wherein the array is raster scanned by linear translation of the stack.

50. An imaging system as claimed in claim 47 wherein the array is raster scanned by rotation about an axis through the stack of emitters and detectors.

51. An imaging system as claimed in claim 47 wherein each emitter and detector is mounted within a self contained housing module.

52. An imaging system as claimed in claim 51 wherein each module is capable of forming a stack with similar modules.

53. An imaging system as claimed in claim 30 wherein only a proportion of the total number of emitters and detectors are in use at any given time.

54. An imaging system as claimed in claim 30 further comprising a signal processor for analyzing the radiation detected by the probe array.

55. An imaging system as claimed in claim 54 further comprising a source of e/m radiation for irradiating the probe array.

56. An imaging system as claimed in claim 55 wherein the source provides a beam of radiation and the system further comprises a series of beam-splitters and fibre couplers, each beam-splitter being arranged to couple a proportion of the beam of radiation via a fibre coupler into an optical fibre such that in use the optical fibre irradiates the probe array.

57. An imaging system as claimed in claim 55 wherein the source provides a beam of radiation and the system further comprises a lensing array, the array being arranged in use to couple a proportion of the beam into an optical fibre such that the fibre irradiates the probe array.

58. An imaging system as claimed in claim 54 wherein the probe array is configured as a hand-held unit and the source and signal processor are housed in a base unit, the hand-held unit and base unit being connected via optical fibre.

\* \* \* \* \*